United States Patent [19]

Willms et al.

[11] Patent Number: 5,022,916
[45] Date of Patent: Jun. 11, 1991

[54] SUBSTITUTED SULFONYLDIAMIDES, PROCESSES FOR THEIR PREPARATION, AND THEIR USE AS HERBICIDES AND PLANT GROWTH REGULATORS

[75] Inventors: Lothar Willms, Hillscheid; Klaus Bauer, Hanau; Hermann Bieringer, Taunus; Helmut Bürstell, Frankfurt am Main, all of Fed. Rep. of Germany

[73] Assignee: Hoechst Aktiengesellschaft, Frankfurt, Fed. Rep. of Germany

[21] Appl. No.: 367,360

[22] Filed: Jun. 16, 1989

[30] Foreign Application Priority Data

Jun. 18, 1988 [DE] Fed. Rep. of Germany ....... 3820647
Jul. 6, 1988 [DE] Fed. Rep. of Germany ....... 3822841

[51] Int. Cl.$^5$ ............... A01N 43/54; A01N 43/66; A01N 43/713; C07D 239/42; C07D 239/28
[52] U.S. Cl. .......................................... 71/92; 71/88; 71/90; 71/93; 544/113; 544/118; 544/122; 544/137; 544/178; 544/180; 544/256; 544/278; 544/279; 544/60; 544/61; 548/262.6
[58] Field of Search ............... 544/320, 330, 332, 122, 544/320, 331, 332; 71/92

[56] References Cited

U.S. PATENT DOCUMENTS

| | | | |
|---|---|---|---|
| 3,931,277 | 1/1976 | Lohaus et al. | 260/543 R |
| 4,419,121 | 12/1983 | Meyer et al. | 71/92 |
| 4,480,101 | 10/1984 | Meyer et al. | 544/320 |
| 4,601,747 | 7/1986 | Willms et al. | 71/92 |

FOREIGN PATENT DOCUMENTS

| | | |
|---|---|---|
| 0039239 A2 | of 0000 | European Pat. Off. |
| 0039239 A3 | of 0000 | European Pat. Off. |
| 0044807 | of 0000 | European Pat. Off. |
| 0070804 | of 0000 | European Pat. Off. |
| 0131258 | of 0000 | European Pat. Off. |
| 2257240 | of 0000 | Fed. Rep. of Germany. |

Primary Examiner—Cecilia Shen
Attorney, Agent, or Firm—Curtis, Morris & Safford, P.C.

[57] ABSTRACT

The present invention relates to compounds of the formula (I) or salts thereof

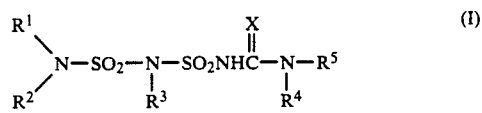

where
$R^1$, $R^2$ or H, are saturated or unsaturated (substituted) aliphatic radicals or (substituted) phenyl, or $R^1$ and $R^2$ together with the N atom by which they are linked are a heterocyclic ring of the formula

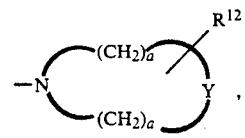

a indices independently of one another being an integer from 1 to 3,
$R^3$ is H, a saturated or unsaturated (substituted) aliphatic radical or a (substituted) phenyl, benzyl or phenethyl radical, or $R^2$ and $R^3$ together are an alkylene chain,
$R^4$ is H, a saturated or unsaturated aliphatic radical or alkoxy, and
$R^5$ is a (substituted) pyrimidinyl, triazinyl, triazolyl or bicyclic, nitrogen-containing heterocyclic radical, which have valuable herbicidal or plant growth-regulating properties.

22 Claims, No Drawings

SUBSTITUTED SULFONYLDIAMIDES, PROCESSES FOR THEIR PREPARATION, AND THEIR USE AS HERBICIDES AND PLANT GROWTH REGULATORS

It is known that heterocyclically substituted N-sulfonamidosulfonylureas have herbicidal and plant-growth regulating properties (EP-A-131,258 or U.S. Pat. No. 4,601,747).

However, the effects of these compounds are not always satisfactory.

Novel heterocyclic N-sulfonyldiamidosulfonamides have now been found which are particularly suitable as herbicides and plant growth regulators.

The present invention therefore relates to compounds of the formula (I) or salts thereof

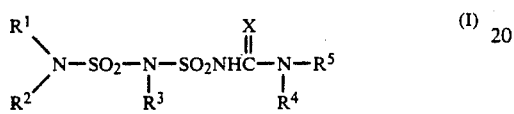
(I)

where
$R^1$ and $R^2$ independently of one another are H, or $(C_1-C_8)$alkyl, $(C_2-C_8)$alkenyl or $(C_2-C_8)$alkynyl, it being possible for these radicals optionally to be monosubstituted or polysubstituted by halogen or monosubstituted or disubstituted by $(C_1-C_4)$alkoxy or $(C_1-C_4)$alkylthio, or are $(C_1-C_4)$alkoxycarbonyl($C_1-C_3$)alkyl, or phenyl which is unsubstituted or monosubstituted or polysubstituted by $(C_1-C_4)$alkyl, $(C_1-C_4)$alkoxy, $(C_1-C_4)$alkylthio, $(C_1-C_4)$alkylsulfinyl or $(C_1-C_4)$alkylsulfonyl, it being possible for the abovementioned radicals to be polysubstituted in the alkyl moiety by halogen or monosubstituted or disubstituted in the alkyl moiety by $(C_1-C_4)$alkoxy, or phenyl which is unsubstituted or monosubstituted or polysubstituted by $(C_1-C_4$alkoxy)carbonyl, halogen or $NO_2$, or $R^1$ and $R^2$ together with the N atom by which they are linked are a heterocyclic ring of the formula

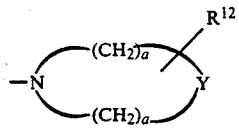

a indicates independently of one another being an integer from 1 to 3,
$R^3$ is H, $(C_1-C_{12})$alkyl, $(C_2-C_8)$alkenyl or $(C_2-C_8)$alkynyl, it being possible for these radicals to be monosubstituted or polysubstituted by halogen or monosubstituted or disubstituted by $(C_1-C_4)$alkoxy or $(C_1-C_4)$alkylthio, or $R^3$ is $(C_1-C_4$alkoxy)carbonyl$(C_1-C_3)$alkyl, or $-(CH_2)_b$phenyl, b being an integer from 0 to 2 and the phenyl radical being unsubstituted or monosubstituted or polysubstituted by $(C_1-C_4)$alkyl, $(C_1-C_4)$alkoxy, $(C_1-C_4)$alkylthio or $(C_1-C_4)$alkylsulfonyl, it being possible for the abovementioned radicals to be monosubstituted or polysubstituted in the alkyl moiety by halogen, or phenyl being substituted by $(C_1-C_4)$alkoxycarbonyl, halogen or $NO_2$, or $R^2$ and $R^3$ together are a $(C_2-C_4)$alkylene chain, is H, $(C_1-C_6)$alkyl, $(C_2-C_8)$alkenyl, $(C_2-C_8)$alkynyl or $(C_1C_4)$alkoxy, $R^5$ is a radical of the formula

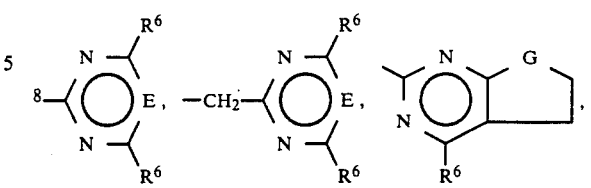

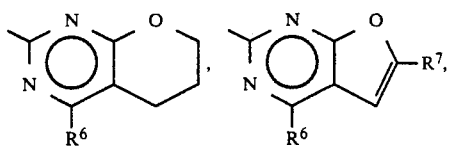

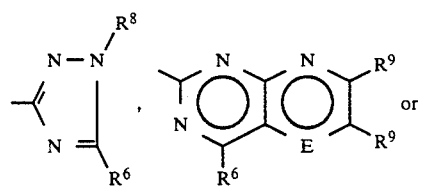

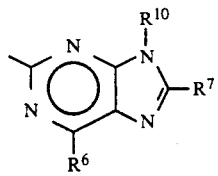

E is CH or N,
G is $CH_2$ or O,
$R^6$ radicals independently of one another are H, halogen, $(C_1-C_6)$alkyl, $(C_1-C_6)$alkoxy or $(C_1-C_6)$alkylthio, it being possible for the abovementioned radicals to be monosubstituted or polysubstituted in the alkyl moiety by halogen or monosubstituted or disubstituted in the alkyl moiety by $(C_1-C_4)$alkoxy or $(C_1-C_4)$alkylthio; or is a radical $N(R^{11})_2$, $(C_3-C_6)$cycloalkyl, $-OCHR^7COOR^{11}$, $(C_2-C_5)$alkenyl, $(C_2-C_4)$alkynyl, $(C_3-C_5)$alkenyloxy or $(C_3-C_5)$alkynyloxy,
$R^7$ is H or $(C_1-C_4)$alkyl,
$R^8$ is $(C_1-C_4)$alkyl, $-CHF_2$ or $-CH_2CF_3$,
$R^9$ radicals independently of one another are H, $(C_1-C_4)$alkyl, $(C_1-C_4)$alkoxy or halogen,
$R^{10}$ is H, $(C_1-C_4)$alkyl, $-CHF_2$ or $-CH_2CF_3$,
$R^{11}$ radicals independently of one another are H, $(C_1-C_4)$alkyl, $(C_2-C_4)$alkenyl or $(C_3-C_4)$alkynyl,
$R^{12}$ is H, $(C_1-C_4)$alkyl, $(C_1-C_4$alkoxy)carbonyl or $(C_1-C_4)$alkoxymethyl,
X is O or S and
Y is O, S, $CH_2$, NH or $N(C_1-C_4)$alkyl.

The compounds of the formula I can form salts in which the hydrogen of the $-SO_2-NH-$ group is replaced by a cation which is suitable for agriculture. In general, these salts are metal salts, in particular alkali metal salts, or alkaline earth metal salts, (optionally alkylated) ammonium salts or organic amine salts. They are preferably prepared from the compounds of the formula I in inert solvents, such as, for example, water, methanol or acetone, at temperatures from 0-100° C. Examples of suitable bases for the preparation of the salts according to the invention are alkali metal carbonates, such as potassium carbonate, or alkali metal hydroxides and alkaline earth metal hydroxides, ammonia or ethanolamine.

Preferred compounds of the formula I are those in which $R^1$ and $R^2$ independently of one another are H or $(C_1-C_4)$alkyl, or $R^1$ and $R^2$ together are a heterocyclic ring of the formula

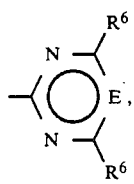

$R^3$ being H, $(C_1-C_6)$alkyl or $(C_2-C_4)$alkenyl,
$R^4$ being H, $(C_1-C_4)$alkyl or allyl,
$R^5$ being a radical of the formula

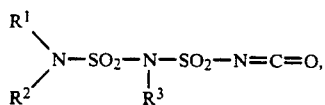

$R^6$ radicals independently of one another being halogen or $(C_1-C_4)$alkyl or $(C_1-C_4)$alkoxy, it being possible for these two to be halogenated,
E being CH or N,
Y being O and a indices being an integer from 1 to 3.

In particular, halogen is F, Cl or Br. In particular, halogenated $(C_1-C_4)$alkyl or halogenated $(C_1-C_4)$alkoxy are $CF_3$, $-CH_2CH_2Cl$, $-CH_2CH_2Br$, $-CH_2CH_2CH_2Cl$, $-CF_2CF_2H$, $-CF_2CFClH$, $-CH_2CHFCH_3$, $-OCHF_2$, $OCF_3$, $OCH_2CF_3$ or $-OCH_2CH_2Cl$.

The present invention furthermore relates to processes for the preparation of the compounds of the general formula (I) or the salts thereof, which comprise
(a) reacting a compound of the formula (II)

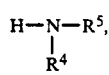

$R^1$, $R^2$ and $R^3$ having the meaning indicated in the case of formula I with the exception of H, with a compound of the formula (III)

$$H-N-R^5,\quad\text{(III)}\\ \phantom{H-N-}R^4$$

or
(b) reacting a compound of the formula (IV)

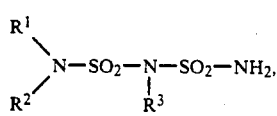

$R^1$, $R^2$ and $R^3$ having the meaning indicated in the case of formula I, with a (thio)carbamate of the formula (V)

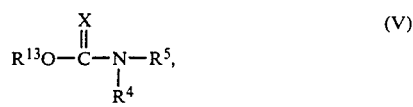

$R^{13}$ being $(C_1-C_6)$alkyl, $(C_1-C_4)$haloalkyl or phenyl which is unsubstituted or monosubstituted or polysubstituted by halogen, $(C_1-C_4)$alkyl or $NO_2$, or
(c) reacting a compound of the formula (VI)

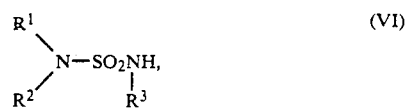

$R^1$, $R^2$ and $R^3$ having the meaning indicated in the case of formula I, with a chlorosulfonylurea of the formula (VII)

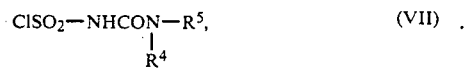

$R^4$ and $R^5$ having the meaning indicated in the case of formula I, and, if desired, converting the compounds obtained by a), b) or c) into their salts.

Process variant a)

The reaction of the compounds (II) and (III) is preferably carried out in inert aprotic solvents, such as, for example, acetonitrile, dichloromethane, toluene, tetrahydrofuran or dioxane, at temperatures between 0° C. and the boiling point of the solvent.

The sulfonediamidosulfonyl iso(thio)cyanates of the formula (II) are novel and, when X is O, may be prepared by reacting chlorosulfonyl isocyanate (VIII) with sulfonyldiamides diamides of the formula (VI) in analogy with the reaction of chlorosulfonyl isocyanate with secondary sulfonamides, which is known from the literature (DE-A 2,257,240 or U.S. Pat. No. 3,931,277), $R^1$, $R^2$ and $R^3$ having the abovementioned meaning with the exception of hydrogen.

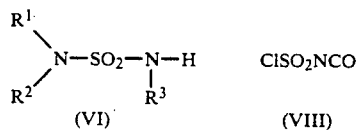

The sulfonyldiamides of the formula (VI) are known or may be prepared by processes which are known in principle, see, for example, Arch. Pharm. 314, 51 (1980), Ann. Chem. 729, 40 (1969), J. Amer. Chem. Soc. 1242 (1944), Chem. Ber. 111, 1915 (1978).

The starting materials of the formula (III) are known or may be prepared by processes which are known in principle, for example by cyclization of appropriate guanidine derivatives with appropriately substituted 1,3-diketones, see, for example "The Chemistry of Heterocyclic Compounds", Vol. XVI (1962) and Supplement I (1970), or by the formation of derivatives of cyanuric chloride, see, for example, "The Chemistry of Heterocyclic Compounds", L. Rapaport: "s-Triazines and Derivatives" (1959).

Process variant b)

The reaction of the compound (IV) with the heterocyclic carbamates of the formula (V) is preferably carried out in the presence of tertiary organic bases, such as, for example, 1,8-diazabicyclo-5,4,0-undec-7-ene (DBU) in inert solvents, such as acetonitrile or dioxane, at temperatures between 20° C. and the boiling point of the solvent (analogously to EP-A 44,807).

The sulfonamides of the formula (IV) which are required for this purpose are novel and may be prepared by reacting the sulfonediamides of the formula (VI) with amidosulfochloride ($ClSO_2NH_2$), $R^1$, $R^2$ and $R^3$ having the meaning mentioned in the case of formula I.

The reaction is carried out in analogy with the reaction of amidosulfochloride with phenols, which is known, it being possible to replace the phenol by the sulfonediamide (VI) with the reaction conditions otherwise remaining identical, see J. Chem. Soc. Perkin I, 678 (1982), Phosphorus and Sulfur Vol. 20, 371 (1984).

The carbamates of the formula (V) are known from the literature or are prepared by known processes (EP-A 70,804).

Process varient c)

The reaction of the compounds (VI) and (VII) is preferably carried out in inert aprotic solvents, such as, for example, acetonitrile, dichloromethane, toluene, tetrahydrofuran or dioxane, at temperatures between −78° C. and the boiling point of the solvent The chlorosulfonylureas of the formula (VII) are known or may be prepared by processes which are known in principle (see, for example, EP-A 39,239).

The compounds according to the invention have an excellent herbicidal activity against a broad range of economically important monocotyledon and dicotyledon weeds. The active substances act equally well on perennial weeds which produce shoots from rhizomes, rootstocks or other perennial organs and which cannot be easily controlled. In this context, it does not matter if the substances are applied before sowing, as a pre-emergence treatment or post-emergence treatment. Some representatives of the moncotyledon and dicotyledon weed flora which can be controlled by the compounds according to the invention may be mentioned individually as examples, but this is not to be taken to mean a restriction to certain species.

The monocotyledon weed species controlled include, for example, Avena, Lolium, Alopecurus, Phalaris, Echinochloa, Digitaria, Setaria etc. and Cyperus species from the annual group, and the perennial species include Agropyron, Cynodon, Imperata and Sorghum etc., and also perennial Cyperus species.

Of the dicotyledon weed species, the range of action covers, for example, Galium, Viola, Veronica, Lamium, Stellaria, Amaranthus, Sinapis, Ipomoea, Matricaria, Abutilon, Sida etc. from the annual plants, and Convolvulus, Cirsium, Rumex, Artemisia etc. from the perennial weeds.

Excellent control of weeds occurring under the specific culture conditions in rice, such as, for example, Sagittaria, Alisma, Eleocharis, Scirpus, Cyperus etc., by the active substances according to the invention is also possible.

If the compounds according to the invention are applied to the soil surface before germination, either emergence of the weed seedlings is prevented completely, or the weeds grow until they have reached the cotyledon stage but growth then comes to a standstill and, after a period of three to four weeks, the plants eventually die completely.

When, in tho post-emergence method, the active substances are applied to the green parts of the plants, growth also stops dramatically very soon after the treatments and the weed plants remain in the growth stage of the time of application, or, after a certain period of time, die more or less rapidly so that competition by the weeds, which is detrimental for the crop plants can thus be prevented at a very early stage and in a sustained manner by using the novel agents according to the invention.

Even though the compounds according to the invention have an excellent herbicidal activity against monocotyledon and dicotyledon weeds, crop plants of economically important crops such as, for example, wheat, barley, rye, rice, maize, sugar beet, cotton and soya beans, are damaged to a negligible extent only, or not at all. Thus, the present compounds are very suitable for selectively controlling undesired plant growth in agricultural plantations of useful plants In addition, the compounds according to the invention have plant growth-regulating properties in crop plants. They engage in the plant metabolism in a regulating manner and can thus be employed for facilitating harvesting, such as, for example, by provoking desiccation, abscission and stunted growth. Furthermore, they are suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The agents according to the invention can be employed in the conventional preparations as wettable powders, emulsifiable concentrates, emulsions, sprayable solutions, dusting agents, seed-dressing agents, dispersions, granules or microgranules. The content of active substance can vary within a wide range and is, as a rule, 2 to 95% by weight, the ideal contents depending on the nature of the formulation.

Wettable powders are preparations which are uniformly dispersible in water and which, besides the active substance, also contain wetting agents, for example, polyoxyethylated alkylphenols, polyoxyethylated fatty alcohols, alkylsulfonates or alkylphenylsulfonates, and dispersing agents, for example sodium ligninsulfonate, sodium 2,2,'-dinaphthylmethane-6,6,'-disulfonate, sodium dibutylnaphthalenesulfonate and also sodium oleoylmethyltaurinate, in addition, if appropriate, to a diluent or inert substance. The formulations are prepared in a customary manner, for example by grinding and mixing of the components.

Emulsifiable concentrates can be prepared, for example, by dissolving the active substance in an inert organic solvent, for example butanol, cyclohexanone, dimethylformamide, xylene and also higher-boiling aromatics or hydrocarbons, with the addition of one or more emulsifiers. In the case of liquid active substances, all or part of the solvent can be omitted. Emulsifiers which can be used are, for example: calcium salts of alkylarylsulfonic acids, such as Ca dodecylbenzenesulfonate or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusting agents are obtained by grinding the active substance with finely divided solid substances, for example talc or natural clays, such as kaolin, bentonite or pyrophillite, or diatomaceous earth.

Granules can be produced either by spraying the active substance onto adsorptive, granulated inert material or by applying active substance concentrates onto the surface of carriers such as sand, kaolinites or of granulated inert material, by means of binders, for example polyvinyl alcohol, sodium polyacrylate or alternatively mineral oils. Suitable active substances can also be granulated in the manner which is conventional for the production of fertilizer granules, if desired in a mixture with fertilizers.

The active substance concentration in wettable powders is, for example, about 10 to 90% by weight; the remainder to 100% by weight is composed of conventional formulation components. In the case of emulsifiable concentrates, the active substance concentration can be about 5 to 80% by weight. Formulations in the form of dusts usually contain 5 to 20% by weight, sprayable solutions about 2 to 20% by weight. In the case of granules, the active substance content depends partly on whether the active compound is liquid or solid and on which granulation auxiliaries, fillers etc., are used.

In addition, the active substance formulations mentioned contain, if appropriate, the adhesives, wetting agents, dispersing agents, emulsifiers, penetrants, solvents, fillers or carriers which are conventional in each case.

These abovementioned formulation types are described, for example, in: Winnacker-Kuchler, "Chemische Technologie [Chemical Technology]", Volume 7, C. Hauser Verlag, Munich, 4th Edition 1986; van Falkenberg, "Pesticide Formulations" Marcel Dekker N.Y., 2nd Ed. 1972–73; K. Martens, "Spray Drying Handbook", 3rd Ed. 1979, G. Goodwin Ltd. London.

Formulation auxiliaries to be used for these formulations (inert materials, emulsifiers, wetting agents, surfactants, solvents etc.) are described in, for example, Marschen, "Solvents Guide", 2nd Ed., Interscience, N.Y. 1950; McCutcheon's "Detergents and Emulsifiers Annual", MC Publ. Corp., Ridgewood N.J.; Sisley and Wood or "Encyclopedia of Surface Active Agents", Chem. Publ. Co. Inc., N.Y. 1964.

For use, the concentrates, present in commercially available form, are diluted, if appropriate, in a conventional manner, for example using water in the case of wettable powders, emulsifiable concentrates, dispersions and, in some cases, also in the case of microgranules. Preparations in the form of dusts and granules and also sprayable solutions are usually not further diluted with other inert substances before use.

The application rate required varies with the external conditions, such as temperature, humidity amongst others. It can vary within wide limits, for example between 0.005 and 10.0 kg/ha or more of active substance; preferably, however, it is between 0.01 and 5 kg/ha.

If appropriate, mixtures or mixed formulations with other active substances, such as, for example, insecticides, acaricides, herbicides, fertilizers, growth regulators or fungicides are also possible.

The following examples illustrate the invention in greater detail.

Formulation Examples

A. A dusting agent is obtained by mixing 10 parts by weight of active substance and 90 parts by weight of talc or inert substance, and comminuting the mixture in a hammer mill.

B. A wettable powder which is readily dispersible in water is obtained by mixing 25 parts by weight of active substance, 64 parts by weight of kaolin-containing quartz as inert substance, 10 parts by weight of potassium ligninsulfonate and 1 part by weight of sodium oleoylmethyltaurinate as wetting and dispersing agent, and grinding the mixture in a pinned-disk mill.

C. A dispersion concentrate which is readily dispersible in water is obtained by mixing 20 parts by weight of active substance with 6 parts by weight of alkylphenol polyglycol ether ($^R$Triton X 207), 3 parts by weight of isotridecanol polyglycol ether (8 EO) and 71 parts by weight of paraffinic mineral oil (boiling range, for example, about 255 to above 377° C.), and grinding the mixture in a ball mill to a fineness of below 5 microns.

D. An emulsifiable concentrate is obtained from 15 parts by weight of active substance, 75 parts by weight of cyclohexanone as solvent and 10 parts by weight of oxyethylated nonylphenol (10 EO) as emulsifier.

EXAMPLE 1

N-[(4,6-Dimethoxy-pyrimidin-2-yl)aminocarbonyl]-N'-(dimethylaminosulfonyl)methylaminosulfonamide a) N,N,N'-Trimethylsulfonyldiamido-N'-sulfonyl isocyanate 28 g (0.20 mol) of chlorosulfonyl isocyanate are dissolved in 300 ml of absolute chlorobenzene, and 25.6 g (0.185 mol) of N,N,N'-trimethylsulfonyldiamide (prepared following Arch. Pharm. 314, 51 (1980)), dissolved in 100 ml of chlorobenzene, are added dropwise at 0° C. The reaction mixture is stirred for 1 hour at 0° C. and heated to reflux temperature for about 2 hours while passing through nitrogen. After the mixture has cooled to room temperature, the liquid is decanted off from the insolubles, and the reaction mixture is concentrated by distillation in vacuo. After thin-layer distillation at 105° C./0.2 mbar, a colorless oil is obtained which is employed in the next stage without further purification.

b) N-[(4,6-Dimethoxy-pyrimidin-2-yl)aminocarbonyl]-N'(dimethylaminosulfonyl)methylaminosulfonamide 3.26 g (0.021 mol) of 2-amino-4,6-dimethoxy-pyrimidine are dissolved in 80 ml of absolute dichloromethane, and 5.10 g (0.021 mol) of N,N,N'-trimethylsulfonyldiamido-N'-sulfonyl isocyanate, dissolved in 20 ml of dichloromethane, are added at 0° C. The mixture is stirred for 1 hour at 0° C., for 18 hours at room temperature and for 2 hours at 40° C. After the reaction mixture has cooled, it is washed twice with 0.5N hydrochloric acid and then with unsaturated solution of common salt. After the crude product has been precipitated using n-heptane, it is recrystallized from CH$_2$Cl$_2$/n-heptane. 6.2 g (74.2% of theory)of N-[(4,6-dimethoxypyrimidin-2-yl)aminocarbonyl]-N'-(dimethylaminosulfonyl)methylaminosulfonamide of melting point 140–142° C. are obtained.

EXAMPLE 2

N-[(4,6-Dimethylpyrimidin-2-yl)aminocarbonyl]-N'-(dimethylaminosulfonyl)methylaminosulfonamide 2.41 g (0.017 mol) of chlorosulfonyl isocyanate are dissolved in 80 ml of absolute acetonitrile and 2.1 g (0.017 mol) of 2-amino-4,6-dimethylpyrimidine are added at −40° C. The reaction mixture is allowed to warm to 0° C. in the course of about 1 hour, and 2.35 g (0.017 mol) of N,N,N'-trimethylsulfonediamide are then added at −40° C. After 2.4 ml (0.017 mol) of triethylamine, dissolved in ml of acetonitrile, have been added, the suspension is allowed to warm to room temperature in the course of about 4 hours. The mixture is stirred for 18 hours at 20° C. and then concentrated in vacuo, taken up in dichloromethane, washed twice with 0.5N hydrochloric acid and twice with a saturated solution of common salt and dried over $Na_2SO_4$, and the dichloromethane solution is concentrated. The crude product is precipitated by adding n-heptane and recrystallizing from dichloromethane/n-heptane. 4.76 g (76.5% of theory) of N-[(4,6-dimethylpyrimidin-2-yl)aminocarbonyl]-N'-(dimethylaminosulfonyl)methylaminosulfonamide of melting point 137–139° C. are obtained.

The compounds of Table 1 below may be prepared in analogy with the preparation procedures described in the above examples.

TABLE 1

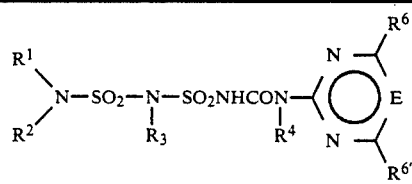

| Ex | $R^1$ | $R^2$ | $R^3$ | $R^4$ | E | $R^6$ | $R^{6'}$ | M.p. |
|---|---|---|---|---|---|---|---|---|
| 3 | H | $CH_3$ | $CH_3$ | H | CH | $CH_3$ | $CH_3$ | |
| 4 | H | $CH_3$ | $CH_3$ | H | CH | $OCH_3$ | $CH_3$ | |
| 5 | H | $CH_3$ | $CH_3$ | H | CH | $OCH_3$ | $OCH_3$ | |
| 6 | H | $CH_3$ | $CH_3$ | H | CH | $OCH_3$ | Cl | |
| 7 | H | $CH_3$ | $CH_3$ | $CH_3$ | CH | $OCH_3$ | $OCH_3$ | 84–88 |
| 8 | H | $CH_3$ | $CH_3$ | H | N | $OCH_3$ | $CH_3$ | |
| 9 | H | $CH_3$ | $CH_3$ | $CH_3$ | N | $OCH_3$ | $CH_3$ | |
| 10 | H | $CH_3$ | $CH_3$ | H | N | $OCH_3$ | $OCH_3$ | |
| 11 | H | $CH_3$ | $CH_3$ | H | N | $OCH_3$ | $NHCH_3$ | |
| 12 | H | $CH_3$ | $CH_3$ | H | CH | $OCH_3$ | $OCH_2CF_3$ | |
| 13 | H | $CH_3$ | $CH_3$ | H | N | $OCH_3$ | $OCH_2CF_3$ | |
| 14 | H | $CH_3$ | $CH_3$ | H | CH | $OCHF_2$ | $CH_3$ | |
| 15 | H | $CH_3$ | $CH_3$ | H | CH | $OCHF_2$ | $OCHF_2$ | |
| 16 | H | $CH_3$ | $CH_3$ | H | N | $OC_2H_5$ | $NHCH_3$ | |
| 17 | H | $CH_3$ | $CH_3$ | H | N | $OCH_3$ | $N(CH_3)_2$ | |
| 18 | H | H | $CH_3$ | H | CH | $OCH_3$ | $OCH_3$ | |
| 19 | H | H | H | H | CH | $OCH_3$ | $OCH_3$ | |
| 20 | $CH_3$ | $CH_3$ | H | H | CH | $OCH_3$ | $OCH_3$ | 182–183° C. |
| 21 | $CH_3$ | $CH_3$ | $CH_3$ | H | CH | $OCH_3$ | $CH_3$ | 162–164° C. |
| 22 | $CH_3$ | $CH_3$ | $CH_3$ | $CH_3$ | CH | $OCH_3$ | $OCH_3$ | 102–104° C. |
| 23 | $CH_3$ | $CH_3$ | $CH_3$ | H | CH | Cl | $OCH_3$ | 142° C. |
| 24 | $CH_3$ | $CH_3$ | $CH_3$ | H | CH | $OCHF_2$ | $OCHF_2$ | |
| 25 | $CH_3$ | $CH_3$ | $CH_3$ | H | CH | Cl | $CH_3$ | |
| 26 | $CH_3$ | $CH_3$ | $CH_3$ | H | CH | $OCH_3$ | $NHCH_3$ | |
| 27 | $CH_3$ | $CH_3$ | $CH_3$ | H | CH | $OCH_3$ | $N(CH_3)_2$ | |
| 28 | $CH_3$ | $CH_3$ | $CH_3$ | H | CH | $OC_2H_5$ | $OCH_3$ | |
| 29 | $CH_3$ | $CH_3$ | $CH_3$ | H | CH | $OCH_3$ | $SCH_3$ | |
| 30 | $CH_3$ | $CH_3$ | $CH_3$ | H | N | $CH_3$ | $CH_3$ | |
| 31 | $CH_3$ | $CH_3$ | $CH_3$ | H | N | $OCH_3$ | $CH_3$ | |
| 32 | $CH_3$ | $CH_3$ | $CH_3$ | H | N | $OCH_3$ | $OCH_3$ | |
| 33 | $CH_3$ | $CH_3$ | $CH_3$ | $CH_3$ | N | $OCH_3$ | $CH_3$ | 69–70° C. |
| 34 | $CH_3$ | $CH_3$ | $CH_3$ | $CH_3$ | N | $OCH_3$ | $OCH_3$ | |
| 35 | $CH_3$ | $CH_3$ | $CH_3$ | H | N | $OCH_3$ | ◁ | |
| 36 | $CH_3$ | $CH_3$ | $CH_3$ | H | N | $OCH_3$ | $NHCH_3$ | |
| 37 | $CH_3$ | $CH_3$ | $CH_3$ | H | N | $OC_2H_5$ | $NHCH_3$ | |
| 38 | $CH_3$ | $CH_3$ | $CH_3$ | H | N | $OCH_3$ | $NHC_2H_5$ | |
| 39 | $CH_3$ | $CH_3$ | $CH_3$ | H | N | $CH_3$ | $SCH_3$ | |
| 40 | $CH_3$ | $CH_3$ | $CH_3$ | H | N | $OCH_3$ | $N(CH_3)_2$ | |
| 41 | $CH_3$ | $CH_3$ | $C_2H_5$ | H | CH | $CH_3$ | H | |
| 42 | $CH_3$ | $CH_3$ | $C_2H_5$ | H | CH | $CH_3$ | $CH_3$ | |
| 43 | $CH_3$ | $CH_3$ | $C_2H_5$ | H | CH | $OCH_3$ | $CH_3$ | |
| 44 | $CH_3$ | $CH_3$ | $C_2H_5$ | H | CH | Cl | $CH_3$ | |
| 45 | $CH_3$ | $CH_3$ | $C_2H_5$ | H | CH | $OCH_3$ | $OCH_3$ | 148–150° C. |
| 46 | $CH_3$ | $CH_3$ | $C_2H_5$ | H | CH | Cl | $OCH_3$ | |
| 47 | $CH_3$ | $CH_3$ | $C_2H_5$ | H | CH | $OCF_2H$ | $OCF_2H$ | |
| 48 | $CH_3$ | $CH_3$ | $C_2H_5$ | $CH_3$ | CH | $OCH_3$ | $OCH_3$ | 130–137° C. |
| 49 | $CH_3$ | $CH_3$ | $C_2H_5$ | H | CH | $OCF_2H$ | $CH_3$ | |
| 50 | $CH_3$ | $CH_3$ | $C_2H_5$ | H | CH | $OCH_3$ | $NHCH_3$ | |
| 51 | $CH_3$ | $CH_3$ | $C_2H_5$ | H | CH | $OCH_3$ | $N(CH_3)_2$ | |
| 52 | $CH_3$ | $CH_3$ | $C_2H_5$ | H | N | $CH_3$ | $CH_3$ | |

TABLE 1-continued $$R^1R^2N-SO_2-N(R^3)-SO_2NHCON(R^4)-\text{ring}(N,E,R^6,R^{6'})$$

| Ex | $R^1$ | $R^2$ | $R^3$ | $R^4$ | E | $R^6$ | $R^{6'}$ | M.p. |
|---|---|---|---|---|---|---|---|---|
| 53 | $CH_3$ | $CH_3$ | $C_2H_5$ | H | CH | $OCH_3$ |  | |
| 54 | $CH_3$ | $CH_3$ | $C_2H_5$ | H | N | $OCH_3$ | $CH_3$ | |
| 55 | $CH_3$ | $CH_3$ | $C_2H_5$ | $CH_3$ | N | $OCH_3$ | $CH_3$ | |
| 56 | $CH_3$ | $CH_3$ | $C_2H_5$ | $CH_3$ | N | $OCH_3$ | $OCH_3$ | |
| 57 | $CH_3$ | $CH_3$ | $C_2H_5$ | H | N | $OCH_3$ | $OCH_3$ | |
| 58 | $CH_3$ | $CH_3$ | $C_2H_5$ | H | N | $OCH_3$ | $OCH_2CF_3$ | |
| 59 | $CH_3$ | $CH_3$ | $C_2H_5$ | H | N | $CH_3$ | $OCH_2CF_3$ | |
| 60 | $CH_3$ | $CH_3$ | $C_2H_5$ | H | N | $OCH_3$ |  | |
| 61 | $CH_3$ | $CH_3$ | $C_3H_7(n)$ | H | CH | $CH_3$ | $CH_3$ | |
| 62 | $CH_3$ | $CH_3$ | $C_3H_7(n)$ | H | CH | $OCH_3$ | $CH_3$ | |
| 63 | $CH_3$ | $CH_3$ | $C_3H_7(n)$ | H | CH | $OCH_3$ | $OCH_3$ | |
| 64 | $CH_3$ | $CH_3$ | $C_3H_7(n)$ | H | CH | Cl | $OCH_3$ | |
| 65 | $CH_3$ | $CH_3$ | $C_3H_7(n)$ | H | N | $OCH_3$ | $CH_3$ | |
| 66 | $CH_3$ | $CH_3$ | $C_3H_7(n)$ | $CH_3$ | CH | $OCH_3$ | $OCH_3$ | 136-138° C. |
| 67 | $CH_3$ | $CH_3$ | $C_3H_7(n)$ | $CH_3$ | CH | $OCH_3$ | $CH_3$ | |
| 68 | $CH_3$ | $CH_3$ | $C_3H_7(n)$ | H | N | $OCH_3$ | $OCH_3$ | |
| 69 | $CH_3$ | $CH_3$ | $-CH(CH_3)_2$ | H | CH | $CH_3$ | $CH_3$ | |
| 70 | $CH_3$ | $CH_3$ | " | H | CH | $OCH_3$ | $CH_3$ | |
| 71 | $CH_3$ | $CH_3$ | " | H | CH | $OCH_3$ | $OCH_3$ | |
| 72 | $CH_3$ | $CH_3$ | " | $CH_3$ | CH | $OCH_3$ | $OCH_3$ | |
| 73 | $CH_3$ | $CH_3$ | " | H | N | $OCH_3$ | $CH_3$ | |
| 74 | $CH_3$ | $CH_3$ | " | H | N | $OCH_3$ | $OCH_3$ | |
| 75 | $CH_3$ | $CH_3$ | $-C_4H_9(n)$ | H | CH | $CH_3$ | $CH_3$ | |
| 76 | $CH_3$ | $CH_3$ | " | H | CH | $OCH_3$ | $CH_3$ | |
| 77 | $CH_3$ | $CH_3$ | " | H | CH | Cl | $OCH_3$ | |
| 78 | $CH_3$ | $CH_3$ | " | H | CH | $OCH_3$ | $OCH_3$ | |
| 79 | $CH_3$ | $CH_3$ | " | $CH_3$ | CH | $OCH_3$ | $OCH_3$ | |
| 80 | $CH_3$ | $CH_3$ | " | H | N | $OCH_3$ | $CH_3$ | |
| 81 | $CH_3$ | $CH_3$ | " | H | N | $OCH_3$ | $OCH_3$ | |
| 82 | $CH_3$ | $CH_3$ | $-CH_2CH(CH_3)_2$ | H | CH | $CH_3$ | $CH_3$ | |
| 83 | $CH_3$ | $CH_3$ | " | H | CH | $OCH_3$ | $OCH_3$ | |
| 84 | $CH_3$ | $CH_3$ | " | H | N | $OCH_3$ | $CH_3$ | |
| 85 | $CH_3$ | $CH_3$ | " | $CH_3$ | N | $OCH_3$ | $OCH_3$ | |
| 86 | $CH_3$ | $CH_3$ | $-(CH_2)_5CH_3$ | H | CH | $OCH_3$ | $OCH_3$ | |
| 87 | $CH_3$ | $CH_3$ | $-(CH_3)_3$ | H | CH | $OCH_3$ | $OCH_3$ | |
| 88 | $CH_3$ | $CH_3$ | $-(CH_2)_9CH_3$ | H | CH | $OCH_3$ | $OCH_3$ | |
| 89 | $CH_3$ | $CH_3$ | $-(CH_2)_{11}CH_3$ | H | CH | $OCH_3$ | Cl | |
| 90 | $CH_3$ | $CH_3$ | $-CH_2CH=CH_2$ | H | CH | $OCH_3$ | $OCH_3$ | |
| 91 | $CH_3$ | $CH_3$ | $-CH_2C\equiv CH$ | H | CH | $OCH_3$ | $OCH_3$ | |
| 92 | $CH_3$ | $CH_3$ | $-CH_2CH=CH(CH_3)$ | H | CH | $OCH_3$ | $OCH_3$ | |
| 93 | $CH_3$ | $CH_3$ | $-CH_2CH_2Cl$ | H | CH | $OCH_3$ | $OCH_3$ | |
| 94 | $CH_3$ | $CH_3$ | $-CH_2CH_2OCH_3$ | H | CH | $OCH_3$ | $OCH_3$ | |
| 95 | $CH_3$ | $CH_3$ | $-CH_2CH_2SCH_3$ | H | CH | $OCH_3$ | $OCH_3$ | |
| 96 | $CH_3$ | $CH_3$ | $-CH_2CH_2SC_2H_5$ | H | CH | $OCH_3$ | $OCH_3$ | |
| 97 | $CH_3$ | $CH_3$ | $-CH_2COOCH_3$ | H | CH | $OCH_3$ | $OCH_3$ | |
| 98 | $CH_3$ | $CH_3$ | $-CH_2COOC_2H_5$ | H | CH | $OCH_3$ | $OCH_3$ | |

TABLE 1-continued $$\begin{array}{c} R^1 \\ | \\ N-SO_2-N-SO_2NHCON \\ | \quad\quad | \quad\quad\quad\quad\quad | \\ R^2 \quad\quad R_3 \quad\quad\quad\quad R^4 \end{array} \text{—(pyrimidine/triazine with } R^6, R^{6'}, E\text{)}$$

| Ex | R¹ | R² | R³ | R⁴ | E | R⁶ | R⁶' | M.p. |
|---|---|---|---|---|---|---|---|---|
| 99 | CH₃ | CH₃ | —CH(CH₃)COOCH₃ | H | CH | OCH₃ | OCH₃ | |
| 100 | CH₃ | CH₃ | —CH₂CH₂COOCH₃ | H | CH | OCH₃ | OCH₃ | |
| 101 | CH₃ | CH₃ | —C₆H₅ | H | CH | OCH₃ | CH₃ | |
| 102 | CH₃ | CH₃ | —C₆H₅ | H | CH | OCH₃ | OCH₃ | |
| 103 | CH₃ | CH₃ | —C₆H₄-2-Cl | H | CH | OCH₃ | OCH₃ | |
| 104 | CH₃ | CH₃ | —C₆H₄-2-CF₃ | H | CH | OCH₃ | OCH₃ | |
| 105 | CH₃ | CH₃ | —C₆H₄-2-SO₂CH₃ | H | CH | OCH₃ | OCH₃ | |
| 106 | CH₃ | CH₃ | —C₆H₄-2-COOCH₃ | H | CH | OCH₃ | OCH₃ | |
| 107 | CH₃ | CH₃ | —C₆H₄-4-Cl | H | CH | OCH₃ | OCH₃ | |
| 108 | CH₃ | CH₃ | benzyl | H | CH | OCH₃ | OCH₃ | |
| 109 | CH₃ | | —(CH₂)₂— | H | CH | CH₃ | CH₃ | |
| 110 | CH₃ | | —(CH₂)₂— | H | CH | CH₃ | OCH₃ | |
| 111 | CH₃ | | —(CH₂)₂— | H | CH | OCH₃ | OCH₃ | 140–142 |
| 112 | CH₃ | | —(CH₂)₂— | H | CH | OCH₃ | Cl | |
| 113 | CH₃ | | —(CH₂)₂— | H | N | OCH₃ | CH₃ | |
| 114 | CH₃ | | —(CH₂)₂— | CH₃ | N | OCH₃ | CH₃ | |
| 115 | CH₃ | | —(CH₂)₂— | H | N | OCH₃ | OCH₃ | |
| 116 | CH₃ | | —(CH₂)₂— | CH₃ | N | OCH₃ | OCH₃ | |
| 117 | CH₃ | | —(CH₂)₂— | H | CH | CH₃ | CH₃ | |
| 118 | CH₃ | | —(CH₂)₂— | H | CH | OCH₃ | OCH₃ | |
| 119 | CH₃ | | —(CH₂)₂— | H | N | OCH₃ | CH₃ | |
| 120a | CH₃ | | —(CH₂)₄— | H | CH | CH₃ | CH₃ | |
| 120b | CH₃ | | —(CH₂)₃— | H | CH | CH₃ | CH₃ | |
| 121a | CH₃ | | —(CH₂)₄— | H | CH | OCH₃ | OCH₃ | |
| 121b | CH₃ | | —(CH₂)₃— | H | CH | OCH₃ | OCH₃ | |
| 122a | CH₃ | | —(CH₂)₄— | H | N | OCH₃ | CH₃ | |
| 122b | CH₃ | | —(CH₂)₃— | H | N | OCH₃ | CH₃ | |
| 123 | C₂H₅ | H | CH₃ | H | CH | OCH₃ | OCH₃ | |
| 124 | C₂H₅ | H | C₂H₅ | H | CH | OCH₃ | OCH₃ | |
| 125 | C₂H₅ | CH₃ | CH₃ | H | CH | OCH₃ | OCH₃ | |
| 126 | C₂H₅ | CH₃ | H | H | CH | OCH₃ | OCH₃ | |
| 127 | C₂H₅ | C₂H₅ | H | H | CH | OCH₃ | OCH₃ | |
| 128 | C₂H₅ | C₂H₅ | CH₃ | H | CH₃ | CH₃ | | |
| 129 | C₂H₅ | C₂H₅ | CH₃ | H | CH | OCH₃ | CH₃ | |
| 130 | C₂H₅ | C₂H₅ | CH₃ | H | CH | OCH₃ | OCH₃ | 116–118° C. |
| 131 | C₂H₅ | C₂H₅ | CH₃ | CH₃ | CH | OCH₃ | OCH₃ | |
| 132 | C₂H₅ | C₂H₅ | CH₃ | H | CH | Cl | OCH₃ | |
| 133 | C₂H₅ | C₂H₅ | CH₃ | H | N | CH₃ | CH₃ | |
| 134 | C₂H₅ | C₂H₅ | CH₃ | H | N | OCH₃ | CH₃ | |
| 135 | C₂H₅ | C₂H₅ | CH₃ | CH₃ | N | OCH₃ | CH₃ | |
| 136 | C₂H₅ | C₂H₅ | CH₃ | H | N | OCH₃ | OCH₃ | |
| 137 | n-C₃H₇ | CH₃ | CH₃ | H | CH | OCH₃ | OCH₃ | |
| 138 | n-C₄H₉ | CH₃ | CH₃ | H | CH | OCH₃ | OCH₃ | |
| 139 | n-C₅H₁₁ | CH₃ | CH₃ | H | CH | OCH₃ | OCH₃ | |
| 140 | n-C₆H₁₃ | CH₃ | CH₃ | H | CH | OCH₃ | OCH₃ | |
| 141 | n-C₈H₁₇ | CH₃ | CH₃ | H | CH | OCH₃ | OCH₃ | |
| 142 | CH₂=CH— | CH₃ | CH₃ | H | CH | OCH₃ | OCH₃ | |
| 143 | CH₂=CHCH₂— | CH₃ | CH₃ | H | CH | OCH₃ | OCH₃ | |
| 144 | CH≡CCH₂— | CH₃ | CH₃ | H | CH | OCH₃ | OCH₃ | |
| 145 | ClCH₂CH₂— | CH₃ | CH₃ | H | CH | OCH₃ | OCH₃ | |
| 146 | CH₃OCH₂CH₂ | CH₃ | CH₃ | H | CH | OCH₃ | OCH₃ | |
| 147 | CH₃SCH₂CH₂— | CH₃ | CH₃ | H | CH | OCH₃ | OCH₃ | |
| 148 | CH₃OOCCH₂— | CH₃ | CH₃ | H | CH | OCH₃ | OCH₃ | |
| 149 | C₂H₅OOCCH(CH₃)— | CH₃ | CH₃ | H | CH | OCH₃ | OCH₃ | |
| 150 | —C₆H₅ | CH₃ | H | H | CH | CH₃ | CH₃ | |
| 151 | —C₆H₅ | CH₃ | CH₃ | H | CH | CH₃ | CH₃ | |
| 152 | —C₆H₅ | CH₃ | CH₃ | H | CH | OCH₃ | CH₃ | |
| 153 | —C₆H₅ | CH₃ | CH₃ | H | CH | OCH₃ | OCH₃ | 30–35° C. |
| 154 | C₆H₅— | CH₃ | CH₃ | H | N | CH₃ | OCH₃ | |
| 155 | C₆H₅— | CH₃ | CH₃ | CH₃ | N | CH₃ | OCH₃ | |
| 156 | C₆H₅ | CH₃ | CH₃ | H | N | OCH₃ | OCH₃ | |
| 157 | —C₆H₄-2-Cl | CH₃ | CH₃ | H | N | OCH₃ | OCH₃ | |
| 158 | —C₆H₄-2-COOCH₃ | CH₃ | CH₃ | H | CH | OCH₃ | OCH₃ | |
| 159 | —(CH₂)₄— | | CH₃ | H | CH | CH₃ | CH₃ | |

TABLE 1-continued $$R^1R^2N-SO_2-N(R_3)-SO_2NHCON(R^4)-\text{ring with } R^6, R^{6'}, E, N$$

| Ex  | R¹                  | R²       | R³       | R⁴  | E  | R⁶   | R⁶'  | M.p.      |
|-----|---------------------|----------|----------|-----|----|------|------|-----------|
| 160 | —(CH₂)₄—            |          | CH₃      | H   | CH | OCH₃ | OCH₃ | 77–80° C. |
| 161 | —(CH₂)₄—            |          | CH₃      | H   | CH | OCH₃ | Cl   |           |
| 162 | —(CH₂)₄—            |          | C₂H₅     | H   | CH | OCH₃ | OCH₃ |           |
| 163 | —(CH₂)₄—            |          | n-C₃H₇   | H   | CH | OCH₃ | OCH₃ |           |
| 164 | —(CH₂)₅—            |          | CH₃      | H   | CH | OCH₃ | OCH₃ |           |
| 165 | —(CH₂)₅             |          | CH₃      | H   | N  | OCH₃ | CH₃  |           |
| 166 | —(CH₂)₅             |          | CH₃      | CH₃ | N  | OCH₃ | OCH₃ |           |
| 167 | morpholin-4-yl      |          | CH₃      | H   | CH | CH₃  | CH₃  |           |
| 168 | ″                   |          | CH₃      | H   | CH | OCH₃ | OCH₃ |           |
| 169 | ″                   |          | CH₃      | H   | CH | OCH₃ | CH₃  |           |
| 170 | thiomorpholin-4-yl  |          | CH₃      | H   | CH | OCH₃ | OCH₃ |           |
| 171 | piperazin-1-yl      |          | CH₃      | H   | CH | OCH₃ | OCH₃ |           |
| 172 | ″                   |          | CH₃      | H   | N  | OCH₃ | CH₃  |           |
| 173 | 4-methyl-piperazin-1-yl |      | CH₃      | H   | CH | OCH₃ | OCH₃ |           |
| 174 | ″                   |          | CH₃      | H   | N  | OCH₃ | CH₃  |           |
| 175 | 2-(COOCH₃)-piperidin-1-yl |   | CH₃      | H   | CH | OCH₃ | OCH₃ |           |
| 176 | 2-(COOC₂H₅)-piperidin-1-yl | | CH₃      | H   | CH | OCH₃ | CH₃  |           |
| 177 | 2-methyl-piperidin-1-yl |     | CH₃      | H   | CH | OCH₃ | OCH₃ |           |
| 178 | 2-(CH₂OCH₃)-piperidin-1-yl | | CH₃      | H   | N  | OCH₃ | CH₃  |           |
| 179 | 3-(COOCH₃)-thiomorpholin-4-yl | | CH₃    | H   | CH | OCH₃ | OCH₃ |           |
| 180 | 3-(COOC₂H₅)-thiomorpholin-4-yl | | CH₃   | H   | CH | CH₃  | CH₃  |           |
| 181 | 2-(COOCH₃)-pyrrolidin-1-yl |  | CH₃      | H   | CH | CH₃  | CH₃  |           |

TABLE 1-continued

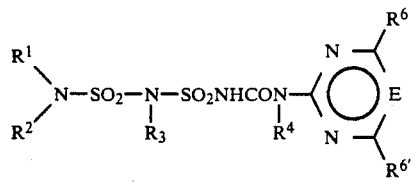

| Ex | R¹ | R² | R³ | R⁴ | E | R⁶ | R⁶' | M.p. |
|---|---|---|---|---|---|---|---|---|
| 182 | ![pyrrolidine-COOC₂H₅] | CH₃ | | H | CH | OCH₃ | OCH₃ | |
| 183 | ![thiazolidine-COOCH₃] | CH₃ | | H | CH | OCH₃ | OCH₃ | |
| 184 | ![thiazolidine-COOC₂H₅] | CH₃ | | H | CH | OCH₃ | OCH₃ | |
| 185 | ![thiazolidine-COOCH₃] | CH₃ | | H | CH | CH₃ | CH₃ | |
| 186 | ![thiazinane-COOC₂H₅] | CH₃ | | H | CH | OCH₃ | OCH₃ | |
| 187 | ![thiazinane-COOC₂H₅] | CH₃ | | CH₃ | CH | OCH₃ | OCH₃ | |

TABLE 2

R¹R²N—SO₂—N(R³)—SO₂NHCONH—R⁵

| Ex | R¹ | R² | R³ | R⁵ | M.p. |
|---|---|---|---|---|---|
| 188 | CH₃ | CH₃ | CH₃ | 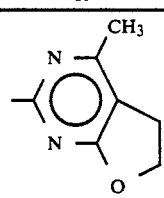 | |
| 189 | CH₃ | CH₃ | C₂H₅ | 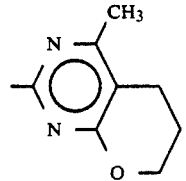 | |
| 190 | CH₃ | CH₃ | C₂H₅ | 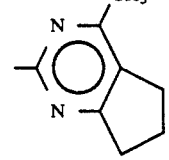 | |
| 191 | CH₃ | CH₃ | CH₃ | 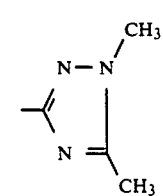 | |

TABLE 2-continued $$R^1\!\!\diagdown_{\!\!\!R^2}\!\!\!\diagup\!N\!-\!SO_2\!-\!\underset{R^3}{N}\!-\!SO_2NHCONH\!-\!R^5$$

| Ex | R¹ | R² | R³ | R⁵ | M.p. |
|---|---|---|---|---|---|
| 192 | CH₃ | CH₃ | CH₃ | (pyrazole with CH₃, OCH₃) | |
| 193 | C₂H₅ | C₂H₅ | CH₃ | " | |
| 194 | —(CH₂)₄— | | CH₃ | " | |
| 195 | —(CH₂)₅— | | CH₃ | " | |
| 196 | CH₃ | —(CH₂)₂— | | " | |
| 197 | CH₃ | —(CH₂)₃— | | " | |
| 198 | CH₃ | CH₃ | CH₃ | (quinazoline-OCH₃) | |
| 199 | CH₃ | CH₃ | CH₃ | (quinazoline-Cl) | |
| 200 | CH₃ | CH₃ | CH₃ | (pyrido-pyrimidine-OCH₃) | |
| 201 | CH₃ | CH₃ | C₂H₅ | (quinazoline-CH₃) | |
| 202 | CH₃ | CH₃ | CH₃ | " | |
| 203 | CH₃ | CH₃ | CH₃ | (benzimidazole-CH₃) | |

Biological Examples

The damage to the weed plants and the tolerance by crop plants were scored using a key where numbers from 0 to 5 express the activity. In this key

- 0 denotes no action
- 1 denotes 0–20% action or damage
- 2 denotes 20–40% action or damage
- 3 denotes 40–60% action or damage
- 4 denotes 60–80% action or damage
- 5 denotes 80–100% action or damage

1. Pre-emergence action on weeds

Seeds or rhizome pieces of monocotyledon and dicotyledon weed plants were placed in plastic pots containing sandy loam soil and covered with soil. Various dosages of aqueous suspensions or emulsions of the compounds according to the invention formulated as wettable powders or emulsion concentrates were then applied to the surface of the cover soil, an application rate of water of 600–800 1/ha (converted).

After the treatment, the pots were placed in the greenhouse and maintained at good growth conditions for the weeds. Visual scoring of the damage to plants or the emergence damage was carried out after the emergence of the test plants after a trial period of 3–4 weeks, comparing them to untreated controls. As shown by the score data in Table 3, the compounds according to the invention have good herbicidal pre-emergence activity against a broad range of weed grasses and weeds.

2. Post-emergence action on weeds

Seeds or rhizome pieces of monocotyledon and dicotyledon weeds were placed in plastic pots in sandy loam ground, covered with soil and grown in the greenhouse under good growth conditions. Three weeks after sowing, the test plants were treated in the three-leaf stage.

Various doses of the compounds according to the invention formulated as wettable powders or as emulsion concentrates were sprayed onto the green parts of the plants, at an application rate of water of 600–800 1/ha (converted), and the action of the preparations was scored visually after the test plants had remained in the greenhouse for about 3–4 weeks under optimum growth conditions, comparing them to untreated controls.

The agents according to the invention also exhibit a good herbicidal activity against a broad range of economically important weed grasses and weeds, when used as a post-emergence treatment (Table 4).

3. Tolerance by crop plants

In further greenhouse experiments, seeds of a relatively large number of crop plants and weeds were placed in sandy loam ground and covered with soil. Some of the pots were treated immediately as described under 1., those remaining were placed in the greenhouse until the plants had developed two to three true leaves and were then sprayed with various dosages of the substances according to the invention as described under 2.

Four to five weeks after application, with the plants remaining in the greenhouse, visual scoring revealed that the compounds according to the invention did not cause any damage to dicotyledon crops, such as, for example, soya beans, cotton, oilseed rape, sugar beet and potatoes, when applied both as a pre-emergence and postemergence treatment, even at high dosages of active substance. Furthermore, Gramineae crops such as, for example, barley, wheat, rye, sorghum millets, maize or rice, were also unaffected by some of the substances. Thus the compounds of the formula I exhibit high selectivity on application for the control of undesired plant growth in agricultural crops.

TABLE 3

Pre-emergence action of the compounds according to the invention

| Example No. | Dosage (kg of a.i/ha) | herbicidal action | | | |
|---|---|---|---|---|---|
| | | SIA | CRS | STM | LOM |
| 1 | 0.6 | 5 | 5 | 5 | 5 |
| 2 | 0.6 | 5 | 5 | 5 | 5 |
| 7 | 0.6 | 5 | 4 | 4 | 5 |
| 20 | 0.6 | 5 | 5 | 5 | 5 |
| 21 | 0.6 | 5 | 5 | 5 | 5 |

TABLE 3-continued

Pre-emergence action of the compounds according to the invention

| Example No. | Dosage (kg of a.i/ha) | herbicidal action | | | |
|---|---|---|---|---|---|
| | | SIA | CRS | STM | LOM |
| 22 | 0.6 | 5 | 5 | 5 | 5 |
| 23 | 0.6 | 5 | 5 | 5 | 5 |
| 33 | 0.6 | 5 | 5 | 5 | 5 |
| 45 | 0.6 | 5 | 5 | 5 | 5 |
| 48 | 0.6 | 5 | 5 | 5 | 5 |
| 66 | 0.6 | 5 | 5 | 5 | 5 |
| 111 | 0.6 | 5 | 5 | 5 | 5 |
| 130 | 0.6 | 4 | 4 | 4 | 4 |
| 153 | 0.6 | 5 | 5 | 5 | 5 |
| 160 | 0.6 | 5 | 5 | 5 | 5 |

TABLE 4

Post-emergence action

| Example No. | Dosage (kg of a.i/ha) | herbicidal action | | | |
|---|---|---|---|---|---|
| | | SIA | CRS | STM | LOM |
| 1 | 0.6 | 5 | 5 | 5 | 5 |
| 2 | 0.6 | 5 | 5 | 5 | 5 |
| 7 | 0.6 | 5 | 5 | 4 | 4 |
| 20 | 0.6 | 5 | 5 | 5 | 5 |
| 21 | 0.6 | 5 | 5 | 5 | 5 |
| 22 | 0.6 | 5 | 5 | 5 | 5 |
| 23 | 0.6 | 5 | 5 | 5 | 5 |
| 33 | 0.6 | 5 | 5 | 5 | 5 |
| 45 | 0.6 | 5 | 5 | 5 | 5 |
| 48 | 0.6 | 5 | 5 | 5 | 5 |
| 66 | 0.6 | 5 | 5 | 5 | 5 |
| 111 | 0.6 | 5 | 5 | 5 | 5 |
| 130 | 0.6 | 4 | 4 | 4 | 4 |
| 153 | 0.6 | 5 | 5 | 5 | 5 |
| 160 | 0.6 | 5 | 5 | 5 | 5 |

Abbreviations:
SIA = *Sinapis alba*
CRS = *Chrysanthemum segetum*
STM = *Stellaria media*
LOM = *Lolium multiflorum*

Growth inhibition of cereals

In dish experiments in the greenhouse, young cereal plants (wheat, barley, rye) in the 3-leaf stage were sprayed with various concentrations of active substance (kg/ha) of compounds according to the invention until dripping wet.

After the untreated control plants had reached a height of about 55 cm, the additional growth was measured on all plants, and the growth inhibition was calculated as a percentage of the additional growth of the control plants. In addition, the phytotoxic effect of the compounds was recorded, 100% denoting that growth had ceased and 0% denoting a growth corresponding to that of the untreated control plants. It was evident that the compounds possess very good growth-regulating properties. The results are compiled in the table below.

TABLE 5

| Compounds of Ex. No. | Application conc. in kg/ha | Growth inhibition (%) | | | Phytotoxic effect |
|---|---|---|---|---|---|
| | | wheat | barley | rye | |
| 1 | 0.62 | 25 | 24 | 43 | no damage |
| | 0.31 | 18 | 17 | 29 | |
| 2 | 0.62 | 19 | 22 | 35 | no damage |
| | 0.31 | 15 | 17 | 29 | |

We claim:
1. A compound of formula I or a salt thereof

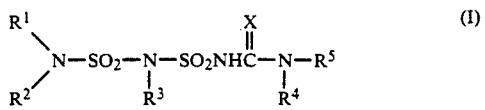

where
R¹ and R² independently of one another are H, or (C₁-C₈)alkyl, (C₂-C₈)alkenyl or (C₂-C₈)alkynyl, it being possible for these radicals optionally to be mono-substituted or polysubstituted by halogen or mono-substituted or disubstituted by (C₁-C₄)alkoxy or (C₁-C₄)alkylthio, or are (C₁-C₄)alkoxycarbonyl(C₁-C₃)-alkyl, or phenyl which is unsubstituted or monosubstituted or polysubstituted by (C₁-C₄)alkyl, (C₁-C₄)alkoxy, (C₁-C₄)alkylthio, (C₁-C₄)alkylsulfinyl or (C₁-C₄)alkylsulfonyl, it being possible for the abovementioned radicals to be polysubstituted in the alkyl moiety by halogen or monosubstituted or disubstituted in the alkyl moiety by (C₁-C₄)alkoxy, or phenyl which is unsubstituted or monosubstituted or polysubstituted by (C₁-C₄alkoxy)carbonyl, halogen or NO₂, or R¹ and R² together with the N atom by which they are linked are a heterocyclic ring of formula

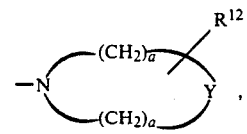

a indices independently of one another being an integer from 1 to 3,
R³ is H, (C₁-C₁₂)alkyl, (C₂-C₈)alkenyl or (C₂-C₈)alkynyl, it being possible for these radicals to be mono-substituted or polysubstituted by halogen or mono-substituted or disubstituted by (C₁-C₄)alkoxy or (C₁-C₄)alkylthio, or R³ is (C₁-C₄alkoxy)carbonyl(C₁-C₃)alkyl, or —(CH₂)ᵦphenyl, b being an integer from 0 to 2 and the phenyl radical being unsubstituted or monosubstituted or polysubstituted by (C₁-C₄)alkyl, (C₁-C₄)alkoxy, (C₁-C₄)alkylthio or (C₁-C₄)alkylsulfonyl, it being possible for the abovementioned radicals to be monosubstituted or polysubstituted in the alkyl moiety by halogen, or phenyl being substituted by (C₁-C₄alkoxycarbonyl, halogen or NO₂, or R² and R³ together are a (C₂-C₄)alkylene chain,
R⁴ is H, (C₁-C₆)alkyl, (C₂-C₈)alkenyl, (C₂-C₈)alkynyl or (C₁-C₄)alkoxy,
R⁵ is a radical of formula

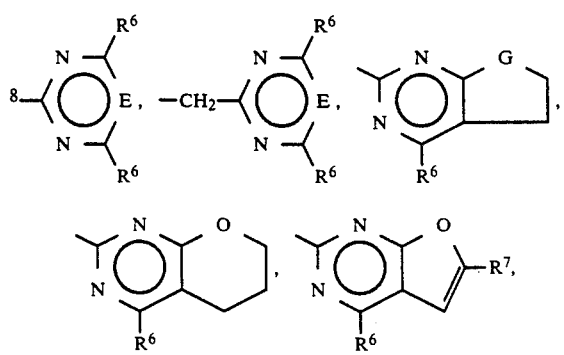

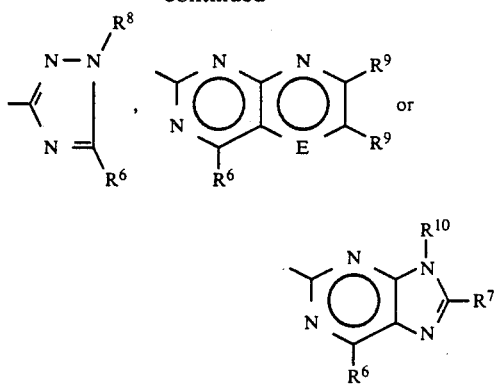

E is CH,

G is $CH_2$ or O, $R^6$ radicals independently of one another are H, halogen, $(C_1-C_6)$alkyl, $(C_1-C_6)$alkoxy or $(C_1-C_6)$alkylthio, it being possible for the abovementioned radicals to be monosubstituted or polysubstituted in the alkyl moiety by halogen or monosubstituted or disubstituted in the alkyl moiety by $(C_1-C_4)$alkoxy or $(C_1-C_4)$alkylthio; or are a radical $N(R^{11})_2$, $(C_3-C_6)$cycloalkyl, $-OCHR^7COOR^{11}$, $(C_2-C_5)$alkenyl, $(C_2-C_4)$alkynyl, $(C_3-C_5)$alkenyloxy or $(C_3-C_5)$alkynyloxy, $R^7$ is H or $(C_1-C_4)$alkyl, $R^8$ is $(C_1-C_4)$alkyl, $-CHF_2$ or $-CH_2CF_3$, $R^9$ radicals independently of one another are H, $(C_1-C_4)$alkyl, $(C_1-C_4)$alkoxy or halogen, $R^{10}$ is H, $(C_1-C_4)$alkyl, $-CHF_2$ or $-CH_2CF_3$, $R^{11}$ radicals independently of one another are.H, $(C_1-C_4)$)alkyl, $(C_2-C_4)$alkenyl or $(C_1-C_4)$alkynyl, $R^{12}$ is H, $(C_1-C_4)$alkyl, $(C_1-C_4$alkoxy)carbonyl or $(C_1-C_4)$alkoxymethyl, X is O or S and Y is O, S, $CH_2$, NH or $N(C_1-C_4)$alkyl.

2. A compound of formula I of claim 1 or a salt thereof where $R^1$ and $R^2$ independently of one another are H or $(C_1-C_4)$alkyl, or $R^1$ and $R^2$ together are a heterocyclic ring of formula

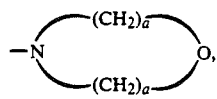

$R^3$ being H, $(C_1-C_6)$alkyl or $(C_2-C_4)$alkenyl, $R^4$ being H, $(C_1-C_4)$alkyl or allyl, $R^5$ being a radical of formula

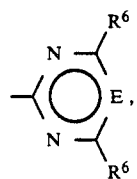

$R^6$ radicals independently of one another being halogen or $(C_1-C_4)$alkyl or $(C_1-C_4)$alkoxy, it being possible for these two to be halogenated, E being CH, and a indices being an integer from 1 to 3.

3. A compound of formula I of claim 1 or a salt thereof, where, in formula I, halogenated $(C_1-C_4)$alkyl is a radical of the group $CF_3$, $-CH_2CH_2Cl$, $-CH_2CH_2Br$, $-CH_2CH_2CH_2Cl$, $-CF_2CF_2H$, $-CF_2CFClH$ or $-CH_2CHFCH_3$, and halogenated $(C_1-C_4)$alkoxy is a radical of the group $-OCHF_2$, $OCF_3$, $OCH_2CF_3$ or $-OCH_2CH_2Cl$.

4. A compound of formula I of claim 1 or a salt thereof, where, in formula I, halogenated $(C_1-C_4)$alkyl is a radical of the group $CF_3$, $-CH_2CH_2Cl$, $-CH_2CH_2Br$, $-CH_2CH_2CH_2Cl$, $-CF_2CF_2H$, $-CF_2CFClH$ or $-CH_2CHFCH_3$, and halogenated $(C_1-C_4)$alkoxy is a radical of the group $-OCHF_2$, $OCF_3$, $OCH_2CF_3$ or $-OCH_2CH_2Cl$.

5. A compound of formula I of claim 1 where, $R^1$, $R^2$ and $R^3$ are $CH_3$;

$R^4$ is H;

$R^5$ is

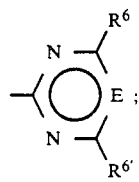

E is CH;

$R^6$ and $R^{6'}$ are $CH_3$; and

X is O.

6. A compound of formula I of claim 1 where, $R^1$ and $R^2$ are $CH_3$;

$R^3$ and $R^4$ are H;

$R^5$ is

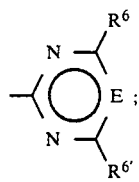

$R^6$ and $R^{6'}$ are $OCH_3$; and

X is O.

7. A compound of formula I of claim 1 where, $R^1$, $R^2$ and $R^3$ are $CH_3$;

$R^4$ is H;

$R^5$ is

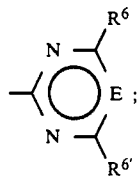

E is CH;

$R^6$ are $OCH_3$; and $R^{6'}$ is $CH_3$; and

X is O.

8. A compound of formula I of claim 1 where, $R^1$, $R^2$, $R^3$ and $R^4$ are $CH_3$;

$R^5$ is

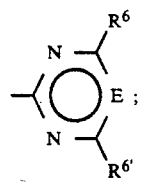

E is CH;
$R_6$ and $R^{6'}$ are $OCH_3$; and
X is O.
9. A compound of formula I of claim 1 where,
$R^1$, $R^2$ and $R^3$ are $CH_3$;
$R^4$ is H;
$R^5$ is

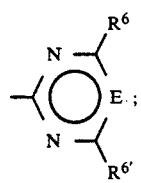

E is CH;
$R^6$ is Cl;
$R^{6'}$ is $OCH_3$; and
X is O.
10. A compound of formula I of claim 1 where,
$R^1$ and $R^2$ are $CH_3$;
$R^3$ is $C_2H_5$;
$R^4$ is H;
$R^5$ is

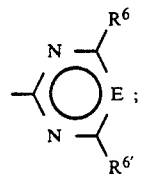

E is CH;
$R^6$ and $R^{6'}$ are $OCH_3$; and
X is O.
11. A compound of formula I of claim 1 where,
$R^1$ and $R^2$ are $CH_3$;
$R^3$ is $C_2H_5$;
$R^4$ is $CH_3$;
$R^5$ is

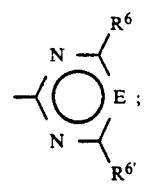

E is CH;
$R^6$ and $R^{6'}$ are $OCH_3$; and
X is O.
12. A compound of formula I of claim 1 where,
$R^1$ and $R^2$ are $CH_3$;
$R^3$ is n-$C_3H_7$;
$R^4$ is $CH_3$;
$R^5$ is

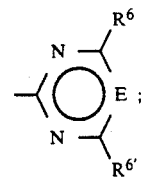

E is CH;
$R^6$ and $R^{6'}$ are $OCH_3$; and
X is O.
13. A compound of formula I of claim 1 where,
$R^1$ are $CH_3$;
$R^2$ and $R^3$ together are $-(C_2)_2-$;
$R^4$ is H;
$R^5$ is

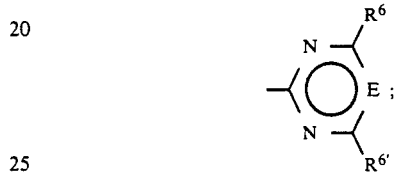

E is CH;
$R^6$ and $R^{6'}$ are $OCH_3$; and
X is O.
14. A compound of formula I of claim 1 where,
$R^1$ is $C_6H_5$;
$R^2$ and $R^3$ is $CH_3$;
$R^4$ is H;
$R^5$ is

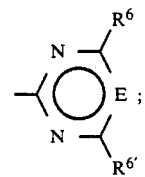

E is CH;
$R^6$ and $R^{6'}$ are $OCH_3$; and
X is O.
15. A compound of formula I of claim 1 where,
$R^1$ and $R^2$ together are $-(CH_2)_4-$;
$R^3$ is $CH_3$;
$R^4$ is H;
$R^5$ is

E is CH;
$R^6$ and $R^{6'}$ are $OCH_3$; and
X is O.
16. A herbicidal agent containing a herbicidally effective amount of a compound of formula I of claim 1, or a salt thereof, and an inert carrier.
17. A plant growth-regulating agent containing a plant growth-regulating effective amount of a compound of formula I of claim 1, or a salt thereof, and an inert carrier.

18. A herbicidal agent containing a herbicidally effective amount of a compound of formula I of claim 2, or a salt thereof, and an inert carrier.

19. A plant growth-regulating agent containing a plant growth-regulating effective amount of a compound of formula I of claim 2, or a salt thereof, and an inert carrier.

20. A method of controlling undesired plants which comprises applying an effective amount of a compound of formula I of claim 1, or a salt thereof, to a plant or an area where said plant is grown.

21. A method of regulating plant growth, which comprises applying an effective amount of a compound of formula I of claim 1, or a salt thereof, to a plant or an area where said plant is grown.

22. The compound which is N-[(4,6-dimethoxypyrimidin-2-yl)aminocarbonyl]-N'-(dimethylaminosulfonyl)-methylaminosulfonamide.

* * * * *